(12) United States Patent
Qian

(10) Patent No.: US 7,186,566 B2
(45) Date of Patent: Mar. 6, 2007

(54) COMBINING TRANSMITTANCE DETECTION AND CHROMATOGRAPHIC STRIP TECHNIQUES FOR QUANTIFICATION OF ANALYTE IN BIOLOGICAL FLUIDS

(76) Inventor: Suyue Qian, 130 Via Dragon, Fremont, CA (US) 94539

( * ) Notice: Subject to any disclaimer, the term of this patent is extended or adjusted under 35 U.S.C. 154(b) by 630 days.

(21) Appl. No.: 10/628,670

(22) Filed: Jul. 28, 2003

(65) Prior Publication Data

US 2005/0026302 A1    Feb. 3, 2005

(51) Int. Cl.
*G01N 33/551* (2006.01)
(52) U.S. Cl. ............... 436/524; 436/518; 436/527; 436/164; 436/169; 422/50; 422/55; 422/56; 422/61; 422/68.1; 435/7.1; 435/283.1; 435/287.1; 435/287.2; 435/287.7; 435/288.7
(58) Field of Classification Search .......... 422/50, 422/55, 56, 57, 59, 61, 68.1, 69, 70, 82.05, 422/82.09; 436/518, 524, 164, 169; 435/283.1, 435/287.1, 287.7
See application file for complete search history.

(56) References Cited

U.S. PATENT DOCUMENTS

| | | | | |
|---|---|---|---|---|
| 5,132,097 A | * | 7/1992 | Van Deusen et al. .... | 422/82.09 |
| 5,968,839 A | * | 10/1999 | Blatt et al. ................ | 436/513 |
| 5,995,236 A | * | 11/1999 | Roth et al. ................ | 356/445 |
| 6,696,240 B1 | * | 2/2004 | Kloepfer et al. .......... | 435/4 |
| 6,780,645 B2 | * | 8/2004 | Hayter et al. ............. | 436/8 |
| 7,008,775 B2 | * | 3/2006 | Martens et al. ........... | 435/7.1 |
| 2002/0192833 A1 | * | 12/2002 | Pan et al. .................. | 436/164 |
| 2004/0219691 A1 | * | 11/2004 | Shartle et al. ............ | 436/518 |
| 2005/0036148 A1 | * | 2/2005 | Phelan .................... | 356/446 |
| 2006/0110283 A1 | * | 5/2006 | Fish ......................... | 422/52 |

* cited by examiner

*Primary Examiner*—Long V. Le
*Assistant Examiner*—Melanie J. Yu

(57) ABSTRACT

Chromatographic strip is used in combination with a transmittance detecting system in a test to quantitate analytes in biological fluid. Chemical reagents or conjugate labels are simply absorbed on the passages' materials of the strip. The substrates, affinity reagents, or antibodies are immobilized on transparent beads in the detection cell of the strip. The biological fluid passes through the strip. The captured analytes are detected by transmittance detection for quantification. Uncaptured elements and interferences in the fluid are drained to the absorbent portion of the strip when the fluid passes the cell as a wash. This chromatographic strip with an analyte capture zone simplifies the procedures that a transmittance detecting system alone cannot overcome. Adjustable light path of the cells in the strip overcome the sensitivity limitation of reflectance detection.

1 Claim, 7 Drawing Sheets

Figure 1:
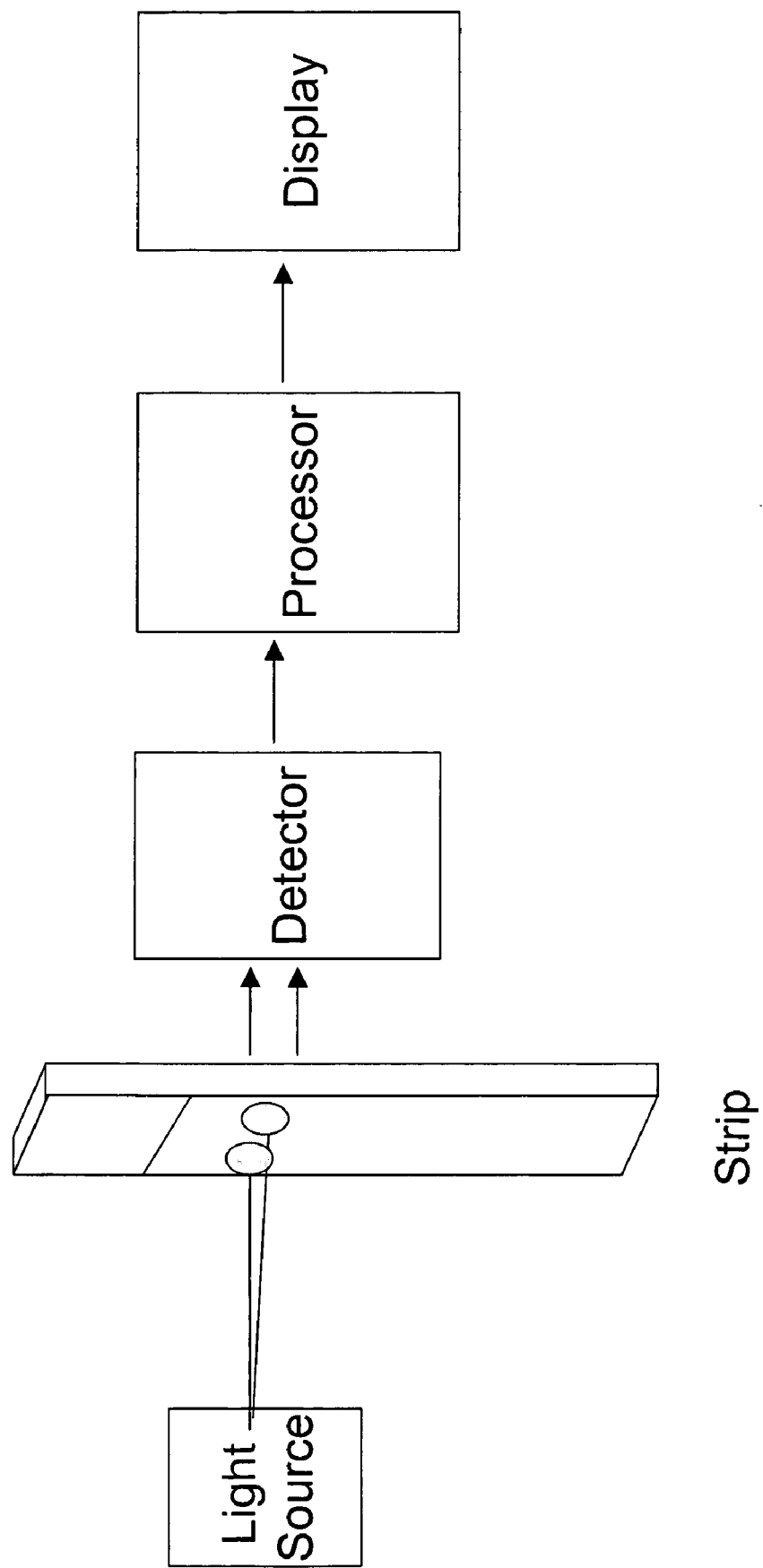

Figure 4. Glycated Hb Measurement Using Chromatographic Strip and Transmittance Detection
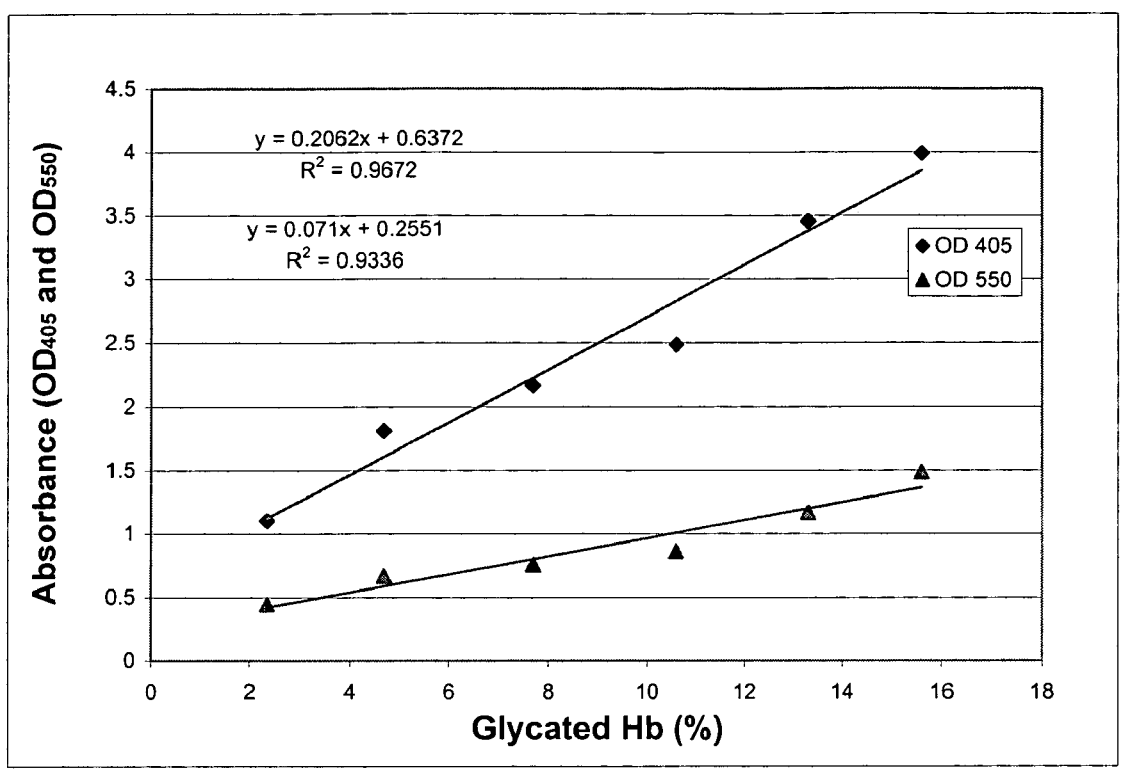

Figure 5. Total Hb Measurement Using Choromatographic Strip and Transmittance Detection
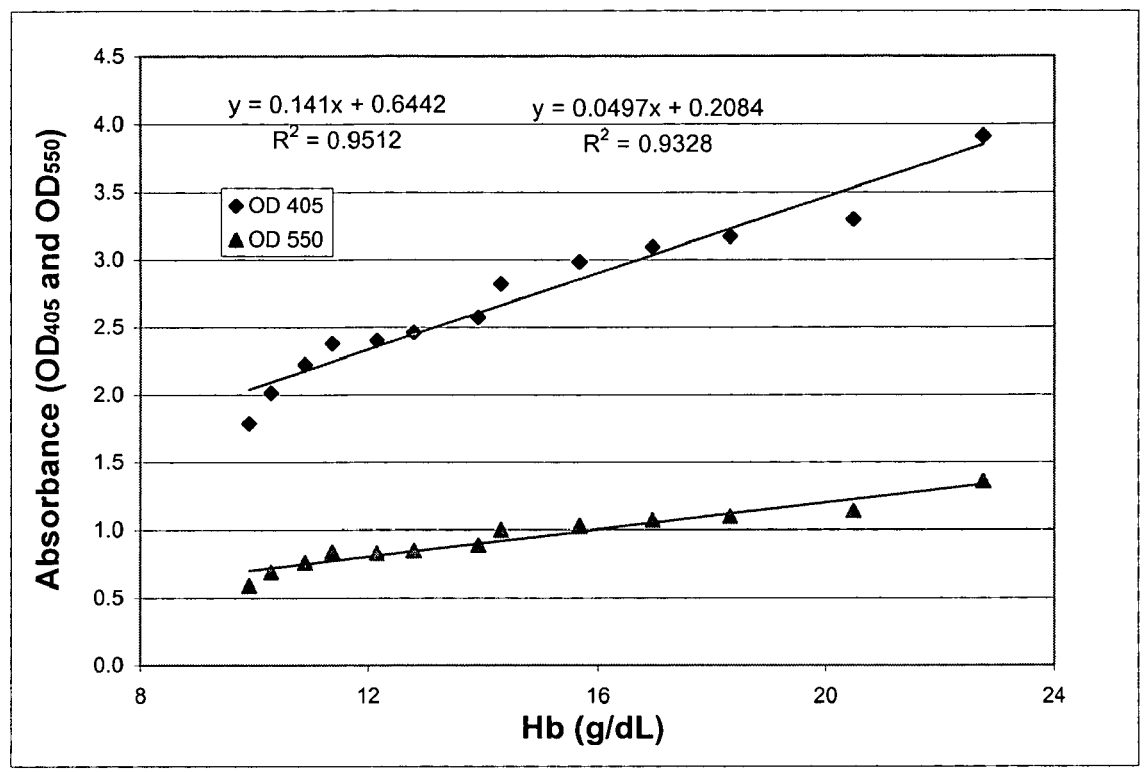

Figure 6. GHb Quantitation by Their Peroxidase Activity
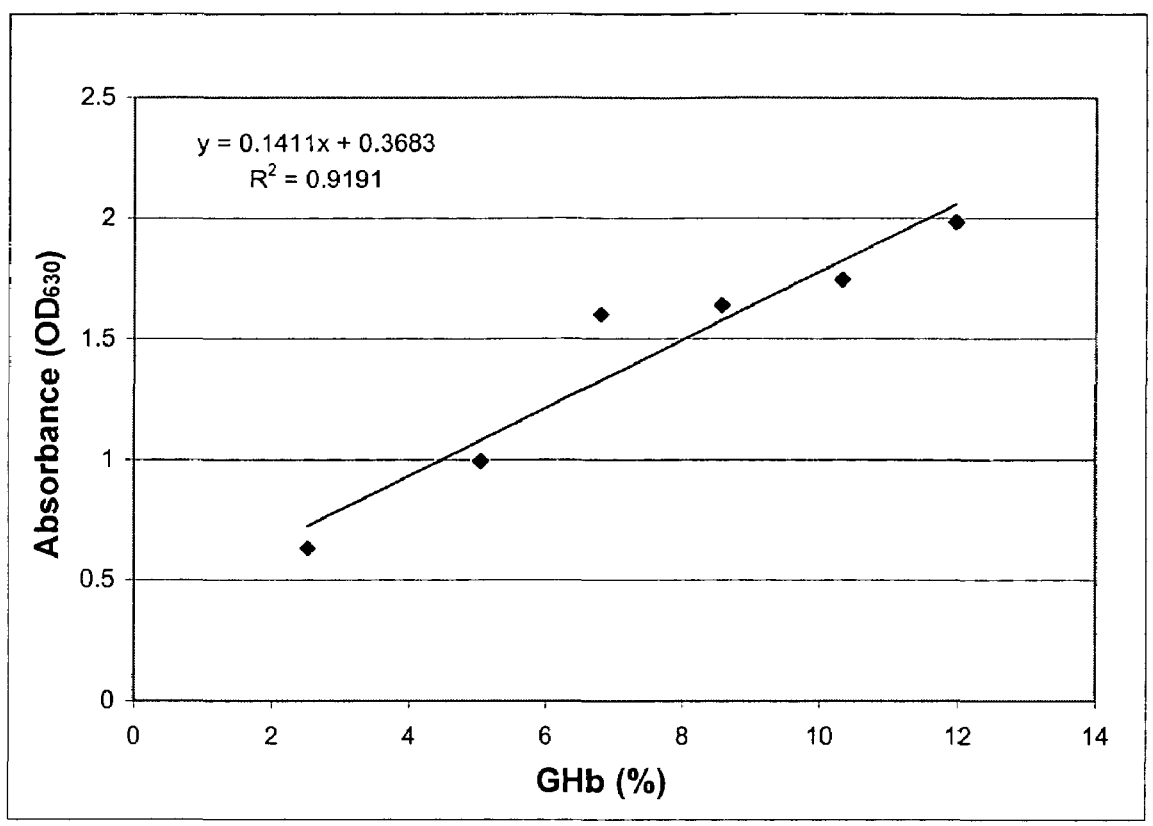

Figure 7. Quantitation of Peroxidase Activity of IgG-HRP Conjugates Using Chromatographic Strip and Transmittance Detection
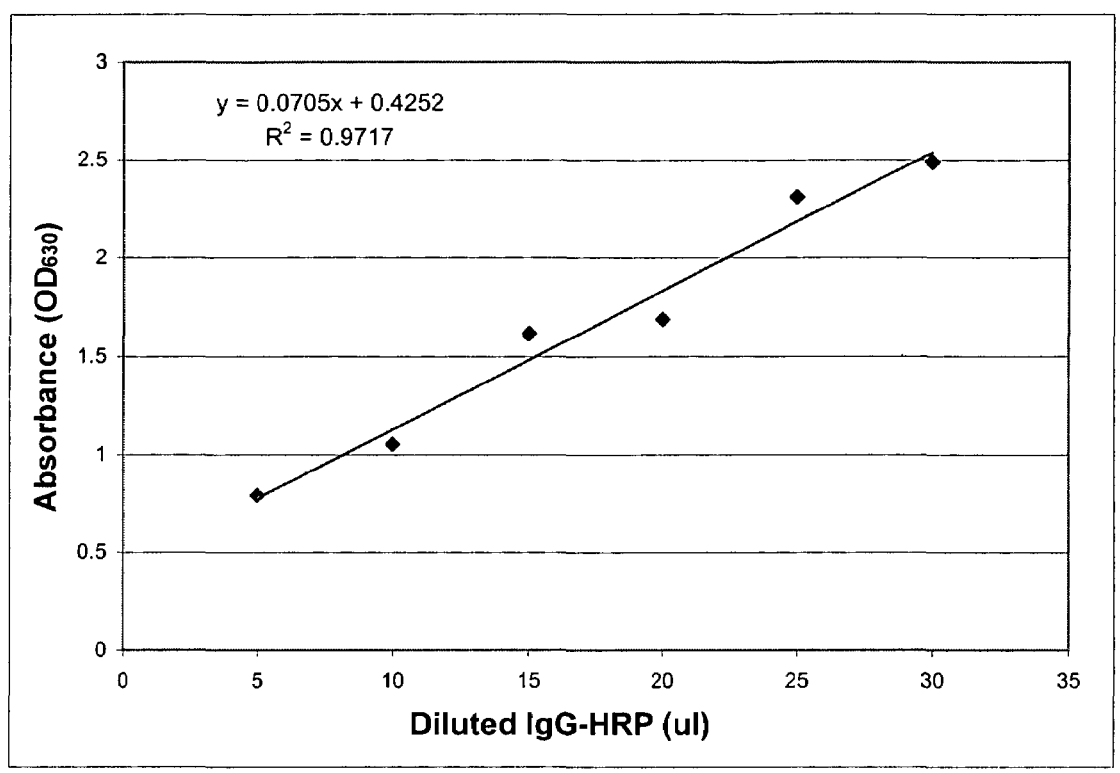

COMBINING TRANSMITTANCE DETECTION AND CHROMATOGRAPHIC STRIP TECHNIQUES FOR QUANTIFICATION OF ANALYTE IN BIOLOGICAL FLUIDS

CROSS-REFERENCE TO RELATED APPLICATION

| | | |
|---|---|---|
| 5451370 | September 1995 | Jones |
| 5213965 | May 1993 | Jones |
| 5589393 | December 1996 | Fiechtner et al.. |
| 5695949 | December 1997 | Galen et al.. |
| 5470752 | November 1995 | Burd et al.. |
| 6399293 B1 | June 2002 | el al.. |
| 5674599 | October 1997 | Saunders et al.. |
| 5972294 | October 1999 | Smith et el.. |
| D417504 | December 1999 | Love et al.. |
| 5654162 | August 1997 | Guire et al.. |
| 5589393 | December 1996 | Fiechtner et al.. |

OTHER PUBLICATIONS

Millipore. "Rapid lateral flow test strips, considerations for product development." Tietz textbook of clinical chemistry by Carl A. Burtis & Edward R. Ashwood, 1994.

BACKGROUND

When lights strike a surface, some lights bounce back and others are absorbed by or transmitted through the media underneath the surface. The light bounced off is reflection. The properties of light reflected, transmitted, and absorbed can be used to measure analyte concentrations.

Many medical instruments use the reflectance principle to detect analytes in a sample, for example the glucose meter from LifeScan, Abbott and Roche; blood analysis and monitoring products by Diavant Reflotron Plus; fructosamine measurement from LXN, while the lipid panel detection system from Cholestech. Reflectance biosensor takes readings from a surface that is covered by an inert porous matrix impregnated with a reagent that interacts with the analyte to produce a light-absorbing product. The operating principle of reflectance detection is as follows: A dry reagent is either immobilized or simply absorbed on an opaque membrane. The reagent reacts with an analyte, giving a product that absorbs the light of certain wavelength. When light strikes on the membrane, the unabsorbed light reflects back to the receiver, yielding an analysis of the properties sought. The amount of lights reflected is inversely proportional to the amount of analytes on the membrane.

Reflectance detection can be used not only in measuring analytes by chemical reaction, but also in immunoassays. In a solid phase competitive immunoassay, an antibody or antigen is immobilized on the membrane. Labeled analytes will compete with free analytes in the sample to bind to the membrane. In a solid phase sandwich assay, a labeled antibody is bound to an analyte, forming a complex, which in turn binds to a capture zone of the membrane where a specific antibody to the analyte is located. In both competitive and sandwich immunoassays, the analytes of interest and interferents are separated as the sample traverses the membrane. Unbound elements are washed through the membrane pores to the absorbent materials. The labeled analytes on the capture zone are readily detected in their natural state by the reflectance method.

Tests using the reflectance principle have several advantages. The most significant one is simplicity, multiple-step tests, like immunoassays, are simplified. The visible signal can be assessed without complicated operations. The tests for HCG, H. Pylori, drug screen, and HbA1c use this principle. These diagnostic tests are simple, quick and easy to use, and therefore have large market in home users and doctor's offices. The tests with reflectance principle, however do have disadvantaged due to the opaque membrane used. Light does not transmit through an ideal opaque membrane. In fact, it will reflect back almost completely to the receiver if no light absorbing product is generated from the analyte-substrate reaction on the membrane. A Thicker membrane absorbs more samples, thereby, increasing the analyte mass absorbed on the membrane, yielding more products, and absorbing more light, therefore less light reflecting back to the receiver. Based on this, increasing membrane thickness can enhance detection. Unfortunately, this potential advantage is negated by a physical limitation. Because of the opacity of the membrane, detection is possible only if light absorbent products are near the membrane surface. However the products are distributed evenly throughout the membrane depth. Any light absorbent products bound deeper than 10 μm under the surface become undetectable, their color being masked by the opaque membrane. Since the visible depth is constant for a given membrane, the impact of increasing the membrane thickness to improve sensitivity has limitations. It is for this reason that the majority of immunoassay tests using reflectance principle are not quantitative, but qualitative. A few immunoassays with reflectance principle are quantitative, but they have narrow separation range, limited sensitivity, and poor performance.

Analytes, such as glucose and cholesterol, have high concentrations in the blood. They range many fold from normal to abnormal levels. These analyte signals are sufficiently high to be measured by the reflectance detecting system, therefore, making sensitivity limitation not an issue in these tests. Unfortunately, in most clinical tests, including therapeutic drug monitoring, tumor markers, cardiac markers, hormones, infectious diseases indexes, autoimmune diseases indexes etc., analytes are low in concentrations. The concentration difference between normal and abnormal is marginal, especially in some drug monitoring tests, such as digitoxin and theophylline. The HbA1c test has a very narrow critical range to determine whether the patient's disease is under control. Some hormones (such as gonadotropines) fluctuate enormously and rapidly. Clearly, a quick, easy, accurate, and sensitive test with expanded testing range is needed for detecting such analytes.

To increase reflectance detecting sensitivity, many inventors use sensitive substrates to amplify the product color intensity through chemical reaction, while others improve the qualities of light sources and detecting systems. All these efforts do not significantly improve sensitivity. In addition, high quality light sources and detecting systems are costly. A system many folds more sensitive than that of current glucose or cholesterol detecting systems is needed for analytes with low concentration or those requiring an expanded separation range.

Tests requiring high sensitivity are usually run with a transmittance detecting system. Its principle is Beer's law. It states: $A = \alpha b c$, where A is absorbance; $\alpha$ is the extinction coefficient absorbent product; b is length of the light path through the light absorbing product in the liquid solution (in cm); and c is the light absorbing product concentration (in moles per liter). Based on Beer's law, increasing the path length of the absorbing product will improve the detecting sensitivity. Transmittance detection is satisfactory for testing analytes with low concentration and narrow separation range, because it detects analytes in the full depth instead of a fraction layer near the surface as the reflectance detecting system does. When analyte concentrations are very low, the signals at different levels can not be distinguished by reflectance detection, but can be differentiated by transmittance detection if the light path through the analyte's product is increased.

Transmittance detecting principle has been widely used in many medical diagnostic systems, such as Roche's Fara/Fara II system, Abbott's Vision system, and Abbott Spectrum system. These systems have developed automated machines to run clinical tests. One example, ELISA (Enzyme-Linked Immuno-Sorbant Assay), is widely used in clinical immunoassays. These tests are performed in the liquid phase and in multiple steps. Technicians running a central clinical laboratory must be trained to operate these automated machines. Patients have to wait at least three to seven days to have testing result back. Promptly providing accurate information on diagnosis is crucial in treating acute diseases. Ideally, operation of the test should be simple, easy, no need trained laboratory technician to run the test. Reliable test results should be obtained in two or three minutes per parameter, so that the patient can be treated without delay. With such an efficient system, many tests currently run in central labs can be tested in small clinics or even at home. Patients will benefit tremendously from this convenience. Such applications will have a huge market. In this patent application, the invention uses a novel strategy to achieve this goal is described.

SUMMARY OF THE INVENTION

Reflectance biosensors have sensitivity limitations. Many clinical tests require an extremely high sensitivity that is far beyond the reflectance biosensor's capability. Then detection principles, such as transmittance, fluorescence, magnetic field, chemiluminescence, and electrochemistry have been widely used. However, these tests procedures are much more complicated, need special equipment, and require well trained technicians. Chromatography is a powerful technique for the separation of biomacromolecules using their specific biological activity or chemical nature. The separation media consists of a ligand attached to an insoluble, inert matrix. When the biological fluid passes through the chromatography media, the analyte will bind to the media while interferents and other proteins will be washed away by the biological fluid as wash. The capture of the analyte by chromatographic media simplifies the test process. When we combine these sensitive detections and simple analyte captures together, the test will have good sensitivity as well as simplicity.

The testing system consists of a dry chromatographic strip and transmittance detecting device. The detection area is filled with transparent beads instead of opaque membrane. Transparent porous materials could be substituted for the beads, but in the following test, only the beads are mentioned. The bead thickness in the detection area can be adjusted to meet the detecting sensitivity requirement. The chemical reagent will be absorbed or bound to the beads. The reactive analyte, when it passes through the detection area, reacts with a chemical reagent on the bead to generate a light-absorbing product of a certain wavelength. The light absorbed is proportional to the analytes in the sample. In the case when an analyte has specific binding sites, the affinity reagent can be immobilized on the beads. The analytes will bind to the affinity reagents on the beads when the sample passes through the beads. Bound analytes can be detected by their absorbance at certain wavelength or by absorbance of their color metric product from reaction with adjacent substrates. In the case of immunoassay, the antibody or antigen also can be immobilized on the beads. The labeled antibodies or antigens impregnated on the passages will flow through the beads, they then bind to their target, and their signals can be detected directly. Indirect detection in immunoassay involves conjugating the enzyme to the antibody or antigen, enzyme labeled antibody or antigen bond on the beads. A color product will be generated by the reaction of the enzyme with its substrate. The light absorption of the product will be read by the transmittance detecting system.

In short, the invention furnishes enormous analytical advantages, including improved precision, expanded detection range, faster testing and most importantly easy use. The transmittance system provides a sensitive detecting capability, which the reflectance system does not. The chromatographic strip simplifies the procedures and achieves the simplicity and reliability as opaque membrane does. For these reasons, this new approach will bring great convenience for home users and small clinics.

DRAWINGS

FIG. 1 Principle of transmittance detection and chromatographic strip

Figure 2B:
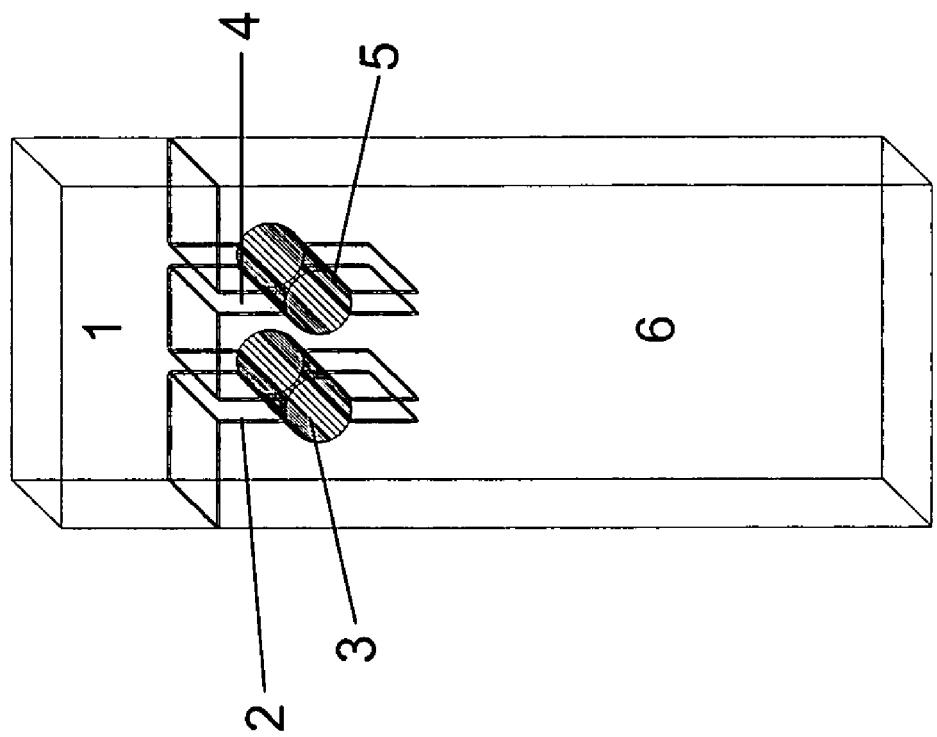
Figure 2A:
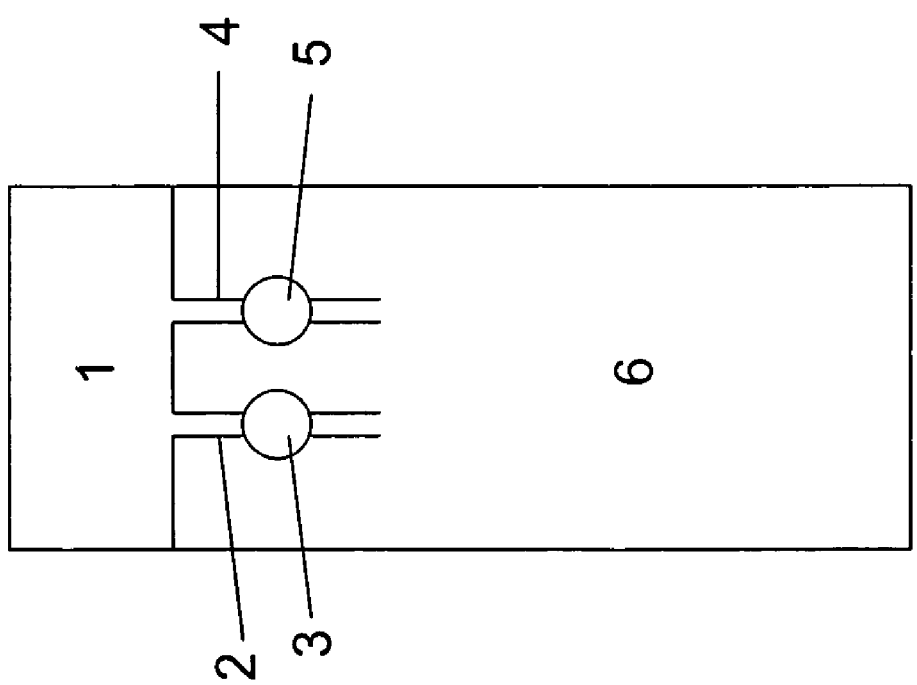

FIG. 2a Front of view of parallel cell arrangement in chromatographic strip

Figures 3A, 3B:
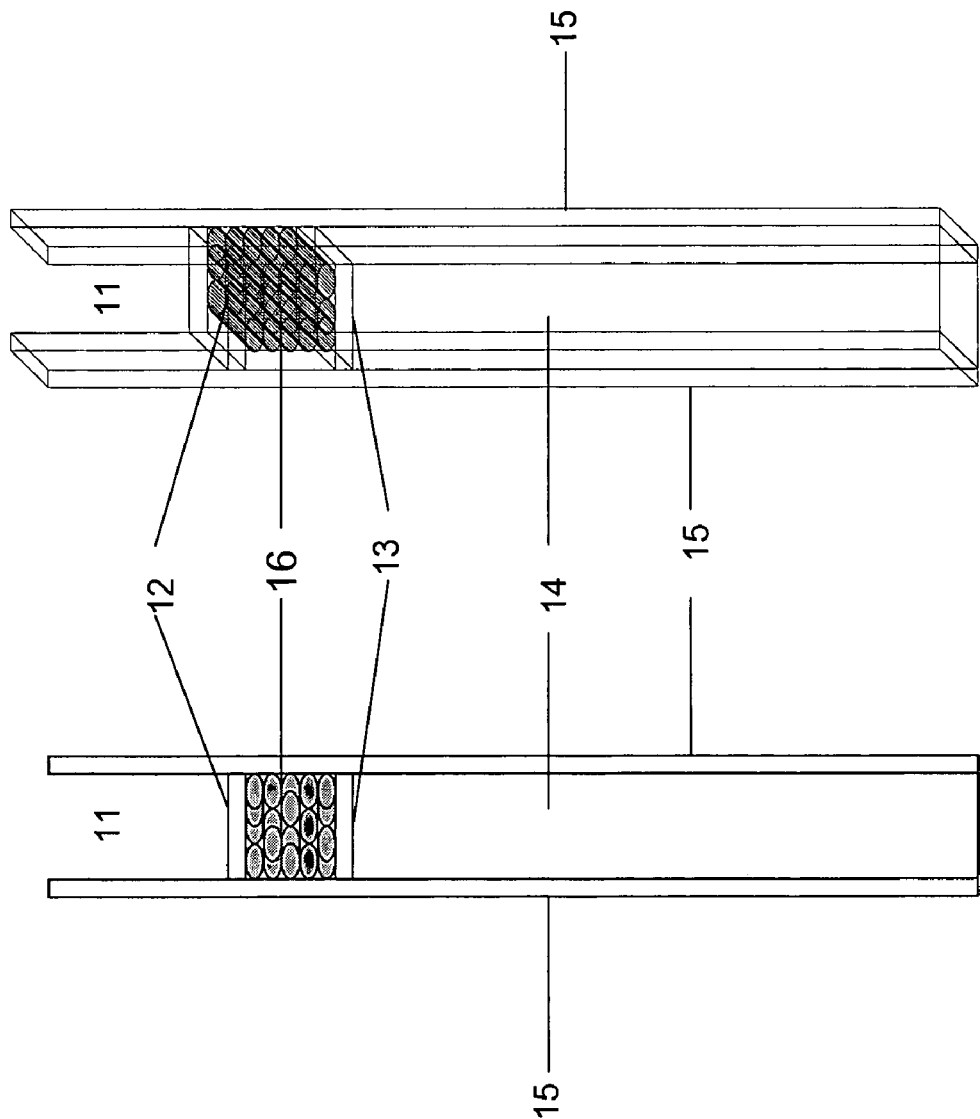

FIG. 2b Three dimensional view of parallel cell arrangement in chromatographic strip FIG. 3a Front of view of test strip used in experiment FIG. 3b Three dimensional view of test strip used in experiment FIG. 4 Glycated hemoglobin measurement using chromatographic strip and transmittance detection FIG. 5 Total hemoglobin measurement using chromatographic strip and transmittance detection FIG. 6 Glycated hemoglobin quantitation by their peroxidase activity using chromatographic strip and transmittance detection FIG. 7 Quantitation of the peroxidase activity of IgG-HRP using chromatographic strip and transmittance detection

STRIP DESIGN AND ANALYTE DETECTION

FIG. 1 is schematic diagram of general principle of the transmittance detection system. Incident light passes through detection cell and reference cell of the strip. The light absorbing product in the cell will absorb the light and the light transmitted will be less than the incident light. The transmitted light is inversely proportional to light absorbing product. The signal will be received, and processed and given final read out result. The whole strip (FIG. 2) has six major components: 1 is sample application well; 2 and 4 are passages; 3 and 5 are the reference cell and detection cell, respectively; 6 is absorbent portion filled with fluid absorbent materials. The frame of the strip can be made from any plastic material or glass. Reference cell 3 and detection cell 5 are filled with light transmittable material for transmittance detection purpose. The detection cell is also named capture zone, which captures analyte in the sample when the sample flows through the cell. The passages 2 and 4 will be filled with materials permeable to fluids. Biological fluid containing analytes will be applied to sample application well 1. The sample flows through passage 2 to reference cell 3, and passage 4 to detection cell 5. There is no fluid communication between passages 2 and 4, or between the cells. The sample flows through to the passages 2 and 4 equally and simultaneously. The materials in the passages do not bind non-specifically to the analytes. The cell dimension and materials used in passages 2 and 4 should control the sample flow speed to provide optimized flow rates, so that reaction in the cells can be completed in desired time periods. The chemical reagent will be absorbed on the materials in the passages 2 and 4, and dried for future application. When a sample is applied to the chromatographic strip, and as it flows through the passages, the reagent will travel to the reference and detection cells, providing an optimized condition for the antibody-antigen interaction, analyte affinity binding or analyte-substrate reaction. The strip can be any shape, fitting into transmittance detecting system. The absorbent materials in the absorbent portion 6 absorb the fluids when the sample flows down to the portion. Openings in the absorbent portion allow the sample to be drained from the cells into the absorbent portion by gravity, preventing back flow from the absorbent portion to the cells. The amount of absorbent materials in the portion should be sufficient to absorb the desired volume of the sample fluids passing through.

The transparent beads in the reference and detection cells can be made from silica, cellulose, cross-linked dextran (sephadex), cross-linked agarose (sepharose), superdex or other suitable materials. Transparent beads could also be polystyrene, polypropylene, polyethylene, Permanox® plastic, glass, styrene, divinylbenzene, polymehtylmethacrylate, polyvinyltoluene, butadiene or vinyltoluene, alone or in combinations. The chemical reagents, affinity reagents, antibodies, antigens, and enzymes can be simply absorbed on the beads in the cells. Alternatively, a variety of functional groups, such as sulfate (—$SO_4$), aldehyde (—CHO), aliphatic amine (—$CH_2$—$NH_2$), amide (—$CONH_2$), aromatic amine (-Ø-$NH_2$), carboxylic acid (—COOH), chloromethyl ($CH_2$—Cl), epoxy (—C—C—O), hydrazide (—CONH—$NH_2$), hydroxyl (—OH), sulfonate (—$SO_3$) and tosyl could be attached to the beads. The functional groups on the beads permit covalent coupling reactions for the stable attachment of the substrates, affinity reagents, enzymes, proteins, antibodies and antigens on the beads. The materials in passages 2 and 4 can be porous plastic, cellulose paper, glass fiber, polytetrafluoroethylene (PTFE), polypropylene, polyester, acrylic copolymer, polyethersulfone, nylon, nitrocellulose, polystyrene, cotton, polyvinylidene fluoride (PVDF), polysulfone, rayon, rayon acetate, polyurethane, polyethylene, filter paper etc.

Direct labels such as colored particles, metallic sols (colloidal gold), dye sols, charged particles, magnetic particles, fluorphors, and colored latex particles are suitable for signal detection. Indirect labels, such as enzymes, e.g. alkaline phosphatase and horseradish peroxidase (HRP) can be used, but they usually require additional substrate immobilized on the beads before a visible signal can be detected.

The reference and detection cells can be circular or any other shape such as retangular, square, oval, trapezoidal, triangular etc. The cells can be any size and thickness suitable for the requirements of the analyte detecting range. The sample flow is directional, and can be vertical or lateral. The sample flow can be generated by gravity, capillary action, wicking, vacuum pump, peristaltic pump, or other means. The detection principle is not limited to transmittance, fluronescence, magnetic field, and chemiluminescence, as well as electrochemistry principles can also be used in combination with their corresponding chromatographic strip.

The light transmission in this application is not exactly like the light transmission in a liquid. When the light passes from one medium to another, such as from a solution to the beads, it bends upon entering the new medium, because part of the wave changes speed before the rest does. The light bending due to a speed change is called refraction. The degree of refraction at the solution-bead interface depends on the amount of analyte collected on the beads and the beads itself. Refraction can result in light loss, if the light is directed away from the detector. The beads and porous materials used in this invention have certain degree surface refraction due to a mismatch in the index of refraction between the solution and the beads. One of the functions of the reference cell is to register the noise due to the light refraction when it passes the solution-bead interface. These noise signals will be subtracted from the signals obtained in the detection cell. To maximize signals detected, one should either use materials having a refractive index close to the solution to reduce the refraction, or fill the space among the beads a material whose refractive index is closer to the beads to reduce the refraction, or design the detecting device at certain angle to collect the refracted light from the beads.

Another potential source of interference is that lights hit non-smooth surface, such as beads, at different angles. Each is reflected at a unique angle. Thus, the reflected lights are scattered in all directions. The light scattering caused by surface irregularity is called diffuse reflection. In the reflectance detecting system, the opaque membrane is very smooth, making the diffuse reflection sufficiently minimal, so that it can be neglected. The beads have an irregular surface. The light undergoes diffusion before it passes through the product. The reference cell will also register the noise due to the light diffuse reflection. Subtraction of the noises from signal is important for corrected detection.

DETAILED DESCRIPTION OF THE INVENTION

General Procedure of the Test

Sample will mix with a buffer. This mixture will then be applied to the sample application well, flowing automatically through the strip. Analytes interested in the sample mixture will be captured on the beads in the detection cell being detected as described above. To make test as one-step test, whole blood will be added to the sample application well. At the bottom of the well is the blood separating materials. The plasma or serum will be separated from the red blood cells. Plasma passes through these cells and is drained to the absorbent portion. The captured analyte reacts with the adjacent substrate on the beads to generate a light absorbing product, which can be detected. Alternatively, no substrate immobilization on the beads is needed if the sample is applied first, and then a buffer containing substrates is added to the well. Such a strategy adds one more step to the testing procedure, but may give less disturbing noise and a clearer background. If direct visible labels are used in the test system, then no substrate is needed. Direct detection of captured labels on the detection cell indicates the relationship with analytes in the sample.

Strip for Competitive Immunoassay

The enzyme labeled analyte will be absorbed on the passages. The enzyme substrate will be absorbed or immobilized on reference and detection cells. Only the detection cells will be coated with an antibody specific to the analyte. When a diluted sample is applied to the well, it will flow through the passages and the analyte will mix with the enzyme labeled analyte on the passage 2 and 4. Both free analytes and the enzyme labeled analytes in the mixture will compete for binding to the antibodies when they flow down to the detection cell. The amount of enzyme labeled analyte captured in the detection cell is inversely proportional to the amount of the analytes in the sample. The enzyme substrate immobilized in the adjacent beads is either oxidized or reduced in the presence of the enzyme to produce a product that absorbs light at predetermined wavelength. The light absorbed in the reference cell will be the background noise. The absorption light in the detection cell is inversely proportional to the analyte amount in the sample. If a visible label to the analyte is used as in the competitive immunoassay. The labeled analytes will simply be absorbed on the passages. After the sample applied to the well, and it flows down to the passages where it mixes with labeled analytes. Mixture of labeled analytes and free analytes will compete for binding to the antibodies on the beads. The absorbance of the labels can be directly detected after they are captured on the beads. The amount of absorbance is inversely proportional to the analyte in the samples.

Strip for Sandwich Immunoassay

Antibody 2-enzyme conjugate will simply be absorbed on the passages. The beads in the detection cell contain enzyme substrate and antibody 1. The beads in the reference cell have only enzyme substrate as reference. As the sample flows down, it mixes with antibody 2-enzyme in the passages. The antibody 2-enzyme will bind to the analyte in the sample to form a complex. As the sample flowing further down, this complex will bind to antibody 1 on the beads in the detection cell, forming a sandwich. The amount of enzyme captured on the beads is proportional to the amount of analytes in the sample. The enzyme substrate near the antibody beads is either oxidized or reduced by the enzyme to produce a product that absorbs light of predetermined wavelength. The light absorbed in the reference cell will be the background noise. The light absorbed in the detection cell is proportional to the amount of analytes in the sample. If a visible label to the analyte is used for the sandwich immunoassay, labeled antibody 2 binds to the analyte to form a complex. The complex then binds the antibody 1 on the beads in the detection cell to form a sandwich. Those labeled antibodies' 2 bind to the analytes in the sample and then bind the antibodies' 1 in the detection cell, presenting a visually detectable color. The absorbance of the labels can be quantitated directly.

Strip for Affinity Reagent-Analyte Binding Assay

The beads in the detection cell will chemically bind the affinity reagent that is specific to the analyte in the sample. The beads in both cells also absorb the analyte specific substrate. When samples pass through the cells, the analytes bind to the affinity reagent on the bead and react with adjacent substrates to generate light-absorbing products. Unbound proteins and interferencts will be washed away as the sample flow to the absorbent portion. Bound analytes can be quantitated by their own light absorbance or by light absorbance of their color metric product.

Strip for Analyte Chemical Reaction Assay

The chemical reagents will be absorbed or immobilized on the beads in the detection cell. The analyte in the sample will react with chemical reagents on the beads when it flows to the detection cell, and producing a light-absorbing product. The amount of the light absorbed can then be read.

EXAMPLES

Test Strip used in the Experiment (One Detection Cell Only, FIG. 3)

The dry strip has a dimension of 1.58×0.35×0.041 inch. Frame 15 of the strip is made with Mellinex plastic. The frame itself is 0.075 inches width each side. The detection cell, that is: capture zone 16 is 0.2×0.2×0.035 inch dimension. Both ends 12 and 13 of the cell are framed with porous plastic from Porex to hold the beads between, but permit fluid flowing through. Both front and back of the strip are glued with a 0.003 inches of Mylar transparent membrane to hold the beads in the detection cell and allow the light transmission through the detection cell. The absorbent pad fills the space of the strip 14 to absorbing fluid. Agarose beads covalently linked with the affinity reagent—boronic acid from Pierce are packed into the detection cell 16.

Experiment 1 (Quantitation of Glycated Hb) The samples from Aalto Scientific were used for this study. The glycated Hb values of used samples first were determined by the Glyco.Gel II method from Pierce. The agorose beads derivatized with 3-aminophenylboronic acids which specifically bind glycated hemoglobins were packed in the detection cell 16. 20 ul of whole blood, containing both glycated hemoglobin and non glycated hemoglobin was applied to the sample application well 11. The blood flowed through top of the porous plastic 12 to the boronate agarose in the detection cell 16. The whole blood was incubated with boronate agarose for 2 min to allow glycated hemoglobin binding to the affinity reagent-boronic acid on the beads. Then 500 ul of the washing buffer (containing 0.25 mM ammonium acetate, 0.05 M $MgCl_2$ at pH 8.05) was applied to the application well 11 to wash away non bound hemoglobin in the detection cell 16 to the absorbent pad 14. Since the heme in the hemoglobin has maximum absorbance at wavelength of 405 and wavelength of 550, the strip was mounted on the frame of the microplate, and the absorbance of the cell 16 was read at wavelength $OD_{405}$ and $OD_{550}$ by microplate reader. Amount of glycated hemoglobin bound on the agorose was proportional to the absorbance (FIG. 4).

Experiment 2 (Total Hb Reading) Hemoglobin concentrations of the blood samples were determined by Drabkin's method from Sigma. Whole bloods with hemoglobin ranging from 9 g/dl to 23 g/dl were diluted 1:20 with the sample buffer (0.25 M ammonium acetate with 0.05 M $MgCl_2$ at pH 8.05). 100 ul of mixture was applied to the sample application well 11 of the strip. The mixture filled the detection cell 16. The cell 16 of the strip was read at $OD_{405}$ and $OD_{550}$ (FIG. 5) same way that the glycated Hb was read. Both total Hb and glycated Hb can be read on this chromatographic strip. The percentage glycated Hb can be calculated.

Experiment 3 (Detection of the Amount of GHb by their Peroxidase Activity) Alternative way to determine the amount of glycated Hb and total Hb is to measure their peroxidase activities. When glycated Hb binds to the beads in the detection cell, the heme in glycated Hb oxidizes or reduces the substrate and produces a visible color product. The product absorbs light at a selected wavelength. The samples with different levels of glycated hemoglobin were diluted with a sample buffer to 1:50,000. The 200 ul of dilution was added to the sample application well, and the strip was further washed with 200 ul of buffer washing away the non bound Hb. 200 ul of TMB membrane peroxidase substrate solution from KPL was applied to the sample well and as it flowed down a color product developed in the cell, which was proportional to the GHb bound to the beads (FIG. 6). The color intensity was determined same way as in experiment 1 and 2.

Experiment 4 (Detection of the Amount of IgG-HRP Conjugates using Chromatographic Strip) A 1:2000 dilution (PBS) of IgG-HRP conjugate (mouse IgG-HRP from Pierce) was prepared. 5, 10, 15, 20, 25, and 30 ul of diluted IgG-HRP conjugate were mixed with 1 ml of PBS respectively. 100 ul of the mixture was applied to the sample well and flowed down to the detection cell. Then 200 ul of the membrane peroxidase substrate-TMB was added to the sample well. A color product developed as the TMB substrate solution flowed through the detection cell to the absorbent part of the strip. The color intensity is proportional to the amount of IgG-HRP conjugate on the bead (FIG. 7).

What is claimed is:

1. A method for detection of analytes in a biological fluid comprising:
    a) providing a dry test strip comprising:
        a sample application well;
        a reference cell and a detection cell;
        a first passage connecting said sample application well to said reference cell;
        a second passage connecting said sample application well to said detection cell;
        an absorbent portion filled with absorbent material, said absorbent portion connected to said reference cell and said detection cell;
        wherein each of said first and second passages are not in fluid communication with each other and each contains a material permeable to fluids and said permeable material in said first and second passages further includes a detection reagent;
        wherein said reference cell contains transparent beads and said detection cell contains transparent beads that are linked with binding partners that are capable of binding with the analyte, wherein the binding partners are selected from ligands, antibodies or antigens;
    b) placing a light source and detection unit on opposite sides of the test strip;
    c) contacting the biological fluid with the sample application well;
    d) allowing the biological fluid to flow through the first and second passageways to provide binding between the analytes and the binding partners in the detection region;
    e) detecting noise produced by said transparent beads in said reference cell by transmittance to provide a first signal;
    f) detecting binding produced by said analyte in said detection cell by transmittance to provide a second signal; and
    g) subtracting said first signal from said second signal thereby determining the amount of analyte in the biological fluid sample.

* * * * *